Aug. 12, 1975 T. HEGG Plant Pat. 3,764
POINSETTIA PLANT
Filed Aug. 19, 1974
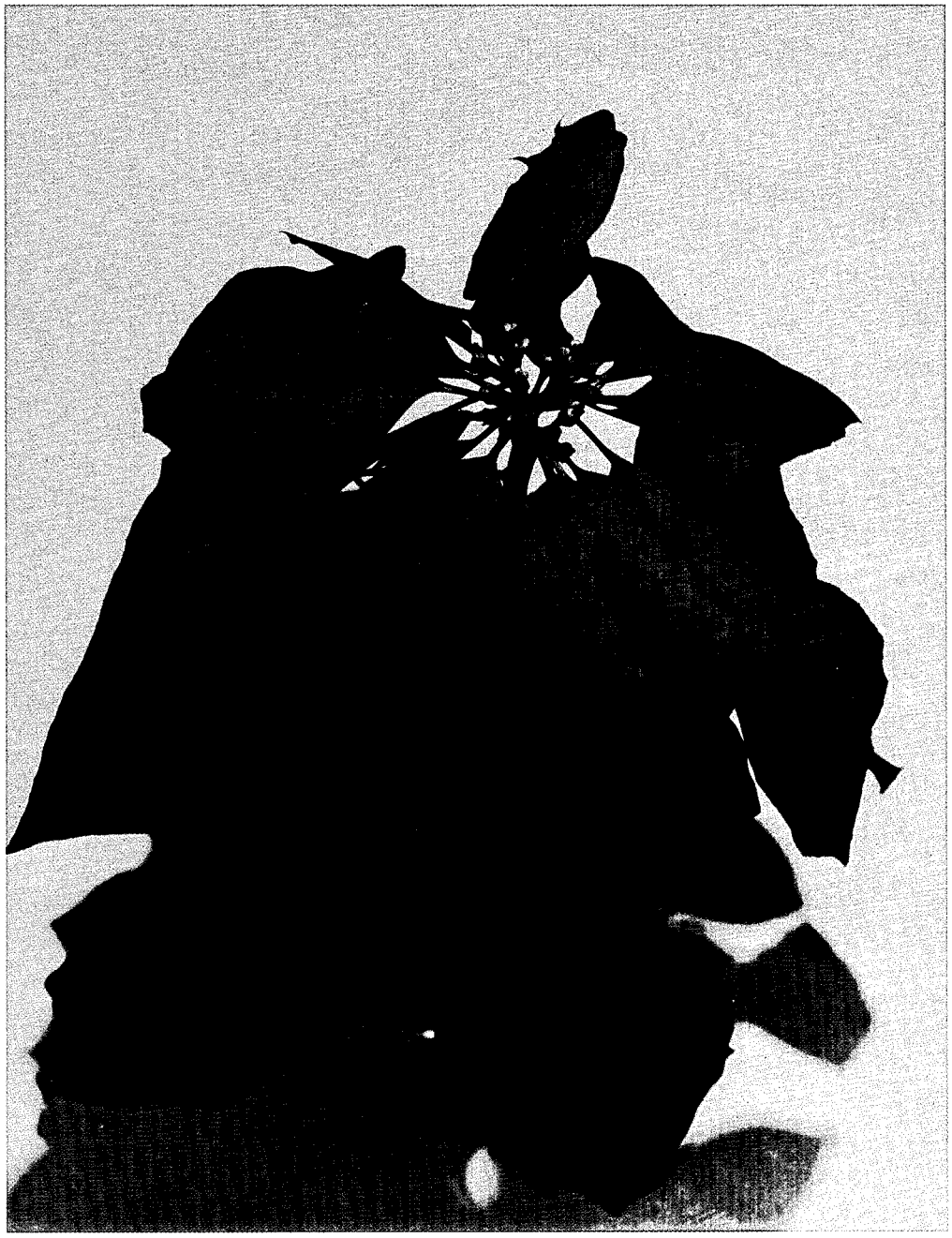

United States Patent

Plant Pat. 3,764

Patented Aug. 12, 1975

1

3,764

POINSETTIA PLANT

Thormod Hegg, Lierbyen, Norway, assignor to Paul Ecke, Jr., Encinitas, Calif.

Filed Aug. 19, 1974, Ser. No. 498,726

Int. Cl. A01h 5/00

U.S. Cl. Plt.—86 1 Claim

The present invention relates to a new and distinct variety of poinsettia plant (botanically known as *Euphorbia pulcherrima*) which was discovered by me as a dark red cultivated sport of the red poinsettia variety known as "Dark Red Annette Hegg" (Plant Pat. No. 3,160), said discovery having been made by me in my greenhouses located at Lierbyen, Norway.

At the time of my discovery aforesaid, I was growing in my greenhouses at Lierbyen various poinsettia varieties, including many plants of the patented variety known as "Dark Red Annette Hegg." In the course of these growing operations, my attention was attracted to one particular plant among those of "Dark Red Annette Hegg" which came into bloom approximately one week earlier than the other plants of "Dark Red Annette Hegg," and which also had a distinctly darker green foliage than the other plants. Close inspection of this particular plant showed that it had sported, so I carefully preserved the sport and kept it under observation. In due course, I asexually reproduced the sport by vegetative cuttings taken therefrom and planted in my greenhouses at Lierbyen. Continued observations and tests of the original sport and its progeny derived from the vegetative cuttings aforesaid and which have been propagated successfully through several generations, fully confirmed that the aforementioned characteristics come true and remain very stable. My observations and tests have further confirmed that for all practical purposes, the new sport generally resembles the parent variety "Dark Red Annette Hegg" except for its darker green foliage and its earlier blooming habit. This earlier blooming feature is very important in commercial production since it achieves substantial savings in greenhouse heating fuel when grown at lower temperatures which are possible when timing the same as its parent "Dark Red Annette Hegg" is desired.

The characteristics and distinctions referred to in the foregoing, among others, represent a unique and commercially valuable combination of features which distinguish this new sport from its parent variety, as well as from all other poinsettia varieties of which I am aware, as evidenced by the following brief summary of principal characteristics which are outstanding in the sport:

(1) A short-growing and compact plant habit;
(2) A uniform and fast rooting habit;
(3) A self-branching habit resulting in the production of multiple blooms without pinching off the terminal buds as required for other poinsettia varieties;
(4) Attractive dark green foliage which is usually somewhat darker green in color than the foliage of "Dark Red Annette Hegg," with the leaves having distinctive petioles of red color on both the upper and lower surfaces thereof;
(5) Attractive dark red bracts, said bracts having less tendency to droop than those of "Dark Red Annette Hegg" when the plants reach maturity, and the dark red color of the bracts being more stable and retaining its brilliance much longer when the plants are used for home decoration; and
(6) Long-lasting plant qualities.

The accompanying drawing shows a typical specimen plant of my new poinsettia as illustrated in color.

Although the details of my new poinsettia sport, except for the principal differences referred to in the foregoing,

2 are generally similar to those described in Plant Pat. No. 3,160, to which reference may be readily had, the following brief description is given for convenience, with color terminology in accordance with Wilson's Horticultural Colour Chart, except where general color terms of ordinary dictionary significance are obvious:

PARENTAGE: Sport of "Dark Red Annette Hegg" (Plant Pat. No. 3,160).

PROPAGATION: Holds its distinguishing characteristics through succeeding propagations by vegetative cuttings.

FORM: Short-growing; compact.

HABIT OF GROWTH: Self-branching; does not require pinching to produce multiple blooms.

ROOTING HABIT: Very uniform and very fast.

BLOOMING HABIT: 8-week variety.

BLOOMING SEASON: Blooms predictably and before Christmas season and beyond; also good for flowering in spring, summer and autumn; usually blooms about one week earlier than "Dark Red Annette Hegg."

FOLIAGE:
- Shape—Similar to "Dark Red Annette Hegg," except more ovate and less serrated.
- Color—Usually much darker green than foliage of "Dark Red Annette Hegg," with petioles of red color on both upper and lower surfaces.

BRACTS: Obovate; relatively broad; retain brilliance longer and less drooping when mature than bracts of "Dark Red Annette Hegg."
- Color—From near Currant Red, Plate 821/3 to near 821.

FLOWERS (CYATHIA): Early; numerous; strong; little if any tendency to split; do not drop off prematurely.

REPRODUCTIVE ORGANS:
- Stamens—Quite numerous; from about ⅛ inch to ¼ inch long. Color—Near Currant Red, Plate 821/2.
- Pollen—Strong. Color—Near Canary Yellow, Plate 2.
- Styles—Color—Near Currant Red, Plate 821/2.
- Ovaries—Color—Near Scheele's Green, Plate 860.
- Nectar cups—Color—Near Buttercup Yellow, Plate 5/1.

GENERAL OBSERVATIONS: While this new sport generally resembles the variety "Dark Red Annette Hegg," it is principally distinguished therefrom by its earlier blooming habit; much darker green foliage color, with leaf petioles which are red on both their upper and lower surfaces; dark red bracts which are more stable and retain their brilliance much longer and with less tendency to fade when grown under the same conditions as "Dark Red Annette Hegg"; and less tendency of the bracts to droop when the plants reach maturity.

I claim:

1. A new and distinct variety of poinsettia plant, substantially as herein shown and described, characterized particularly as to novelty by its general similarity to the variety "Dark Red Annette Hegg" (Plant Pat. No. 3,160), but being principally distinguished therefrom by its earlier blooming habit, much darker green foliage color, dark red bracts which are more stable and retain their brilliance much longer and with less tendency to fade when grown under the same conditions as "Dark Red Annette Hegg," and less tendency of the bracts to droop when the plants reach maturity.

References Cited

UNITED STATES PATENTS

| | | | |
|---|---|---|---|
| P.P. 2,962 | 1/1970 | Hegg | Plants—86 |
| P.P. 3,160 | 5/1972 | Ecke | Plants—86 |
| P.P. 3,392 | 8/1973 | Ecke | Plants—86 |
| P.P. 3,394 | 8/1973 | Ecke | Plants—86 |

ROBERT E. BAGWILL, Primary Examiner